US006809118B2

(12) United States Patent
Chung

(10) Patent No.: US 6,809,118 B2
(45) Date of Patent: Oct. 26, 2004

(54) METHODS FOR THERAPY OF RADIATION CUTANEOUS SYNDROME

(76) Inventor: Yih-Lin Chung, 3F, No. 18, Lane 160, Swei Rd., Daan Chiu, Taipei (TW)

(*) Notice: Subject to any disclaimer, the term of this patent is extended or adjusted under 35 U.S.C. 154(b) by 18 days.

(21) Appl. No.: 10/205,738

(22) Filed: Jul. 25, 2002

(65) Prior Publication Data

US 2004/0018958 A1 Jan. 29, 2004

(51) Int. Cl.[7] ........................ A61K 31/19; A61K 31/20; A61K 7/48; A61K 7/42; A61K 7/44

(52) U.S. Cl. ........................ 514/570; 514/575; 514/557; 514/559; 424/59; 424/60; 424/886; 424/887; 424/925; 424/928

(58) Field of Search ................................ 514/570, 575, 514/557, 559; 424/59, 60, 886, 887, 925, 928

(56) References Cited

U.S. PATENT DOCUMENTS 6,538,030 B2 * 3/2003 Chung et al. ............... 514/570
2002/0055542 A1 * 5/2002 Chung et al. ............... 514/570
2002/0183388 A1 * 12/2002 Gudas et al. ............... 514/559

OTHER PUBLICATIONS

ADR news, Phenytoin. Stevens–Johnson syndrome: case report, Serious Reactions (ADR news), Feb. 22, 1996, ADISNEWS. See: abstract.*

Merck Index, Ninth Edition, 1976, pp. 137 and 1273.*

U.S. patent application Ser. No. 09/938,926, Chung et al.

* cited by examiner

*Primary Examiner*—Frederick Krass
*Assistant Examiner*—Clinton Ostrup
(74) *Attorney, Agent, or Firm*—Fish & Richardson P.C.

(57) ABSTRACT

Compounds of a histone deacetylase inhibitor. The compounds are capable of simultaneously stimulating epithelium regrowth, inhibiting cutaneous fibroblast proliferation, decreasing collagen deposit, suppressing fibrogenic growth factor and subsiding inflammatory cytokine, and are useful inhibiting the main features of radiation cutaneous syndrome. Results include a decrease in skin swelling, promotion of epithelium healing, and prevention of cutaneous fibrosis, ulceration and necrosis. The present invention provides methods of treating, preventing or ameliorating radiation-induced skin damage by administering a therapeutically effective amount of a histone deacetylase inhibitor.

13 Claims, 11 Drawing Sheets

METHODS FOR THERAPY OF RADIATION CUTANEOUS SYNDROME

BACKGROUND OF THE INVENTION

1. Field of the Invention

The present invention relates to a pharmaceutical composition and method for the treatment of radiation cutaneous syndrome. More particularly, the present invention relates to a pharmaceutical composition and method for the treatment of skin reaction involving swelling, desquamation, ulceration, fistula and fibrosis due to radiation exposure or radiotherapy.

2. Description of the Related Art

Radiotherapy is an effective modality for head and neck, skin, anogenital and breast cancers. However, the radiation-induced skin damage collectively termed radiation cutaneous syndrome including acute skin reactions involving swelling, desquamation and ulceration, and late cutaneous fibrosis and fistual limit the therapeutic ration. In addition, the skin is affected in every form of external radiotherapy of internal organs. Application of steroidal or nonsteroidal anti-inflammatories has unsatisfactory results and toxicities. An approach to selectively reduce skin morbidity without compromising tumor mortality by radiotherapy is needed.

The course of radiation cutaneous syndrome follows a distinct pattern. The manifestation stage is characterized by erythema and discrete scaling within hours to days followed by subepidermal swelling and blistering within days to weeks, and then progressing to epidermal atrophy, teleangiectasia and fibrosis within months to years, or even ulceration and fistula formation in severe cases. In chronic forms, cutaneous fibrosis is commonly seen. It is caused by an increased production of collagen fibers in the cutaneous and subcutaneous tissues, which can lead to functional impairment of the affected area, and result in contractures, damage of lymph vessels, and the secondary ulceration. Moreover, a variety of cytokines are locally upregulated following radiation to the skin. Induction of cytokines may be responsible for the early and longer-term side effects on skin after irradiation. Inhibition of TNF-α has been shown to ameliorate the acute inflammation and skin ulcer. The critical role of the TGF-β in late radiation fibrosis has been proposed as a major target of antifibrotic agents. Thus, simultaneously stimulating the growth of epithelial cells, inhibiting the proliferation of cutaneous fibroblasts, and modulating the fibrogenic growth factors may provide an effective method to reduce skin toxicity in acute and late radiation damage.

SUMMARY OF THE INVENTION

According to the present invention it was surprisingly found that histone deacetylase inhibitors and in particular valproic acid, trichostatin A and phenylbutyrate strongly inhibit the main features of radiation cutaneous syndrome, resulting in decrease of skin swelling, promotion of desquamation healing, and prevention of cutaneous fibrosis. That simultaneously epithelium regrowth is stimulated, cutaneous fibroblast proliferation is inhibited, collagen deposit is decreased, and fibrogenic growth factor (TGF-beta) and the proinflammatory cytokine (TNF-alpha) are suppressed all indicate that valproic acid, trichostatin A and phenylbutyrate are potent agents for the treatment of radiation cutaneous syndrome.

The present invention is directed to the use of a histone deacetylase inhibitor and a pharmaceutically acceptable carrier or a pharmaceutically acceptable salt thereof for the preparation of a pharmaceutical composition for the treatment of radiation cutaneous syndrome.

Histone deacetylase inhibitors are substances causing an inhibition of the activity of histone deacetylases, resulting in hyperacetylation. Currently compounds shown to inhibit the activity of histone deacetylase fall into six structurally diverse classes, comprising: phenylbutyrate of the short chain fatty acid class, depudecin of the epoxide class, trapoxin A of the cyclic tetrapeptide class containing a 2-amino-8-oxo-9,10-epoxy-decanoyl moiety, depsipeptide of the cyclic tetrapeptide class lacking a 2-amino-8-oxo-9,10-epoxy-decanoyl moiety, trichostatin A of the hydroxamic acid class, and the benzamide class.

Phenylbutyrate inhibits histone deacetylases by a non-competitive mechanism at millimolar concentrations. Trichostatin A is a specific inhibitor of histone deacetylase, and effective in the submicromolar range.

BRIEF DESCRIPTION OF THE DRAWINGS

The present invention will be more fully understood and further advantages will become apparent when reference is made to the following description of the invention and the accompanying drawings in which:

FIGS. 2*a*–2*c* are of normal skin; FIGS. 2*d*–2*f* are of acute reaction on Day 7 after irradiation, showing subepithelial swelling. FIGS. 2*g*–2*i* are of the vehicle group on Day 60, showing thinner epithelium, subepithelium swelling, increased vessel and skin appendage density, and thick dermis with more collagen deposit. FIGS. 2*j*–2*l* are of the histone deacetylase inhibitor treated group on Day 60, showing thickness of epithelium, no collagen accumulation, and no vessel and appendage proliferation. 2*a*, 2*d*, 2*g* and 2*j* are H&E histology at 40× field. 2*b*, 2*e*, 2*h* and 2*k* are H&E histology at 100× field. 2*c*, 2*f*, 2*i* and 2*l* are H&E histology at 200× field.

FIG. 3*a* is a picture of acute dermatitis on Day 7, showing that TGF-beta was upregulated after irradiation; FIG. 3*b* is of the vehicle group on Day 60, showing that the expression of TGF-beta after irradiation was increased with time, persistent and highly expressed in fibrogenic skin both in keratinocytes of the epidermis and in myofibroblasts of the dermis; FIG. 3*c* is of the treated-group on Day 60, showing that the histone deacetylase inhibitor suppressed the TGF-beta expression effectively, which correlates well with less collagen fiber accumulation in dermis and more cell layers in epithelium since TGF-beta triggers fibroblast proliferation but inhibits epithelial cell growth.

FIG. 4*a* is a picture of chronic ulceration with necrosis and bullae formation of the epidermis near the ulcer (an example of severe radiation skin damage on Day 130), showing that TNF-α was upregulated in the subcutaneous tissue with ulcerations after irradiation. FIG. 4*b* is of the treated-group on Day 130, showing that the histone deacetylase inhibitor suppressed the TNF-α expression effectively, which correlates well with less lymphocyte infiltration and no chronic ulceration.

DETAILED DESCRIPTION OF THE INVENTION

Figure 1:
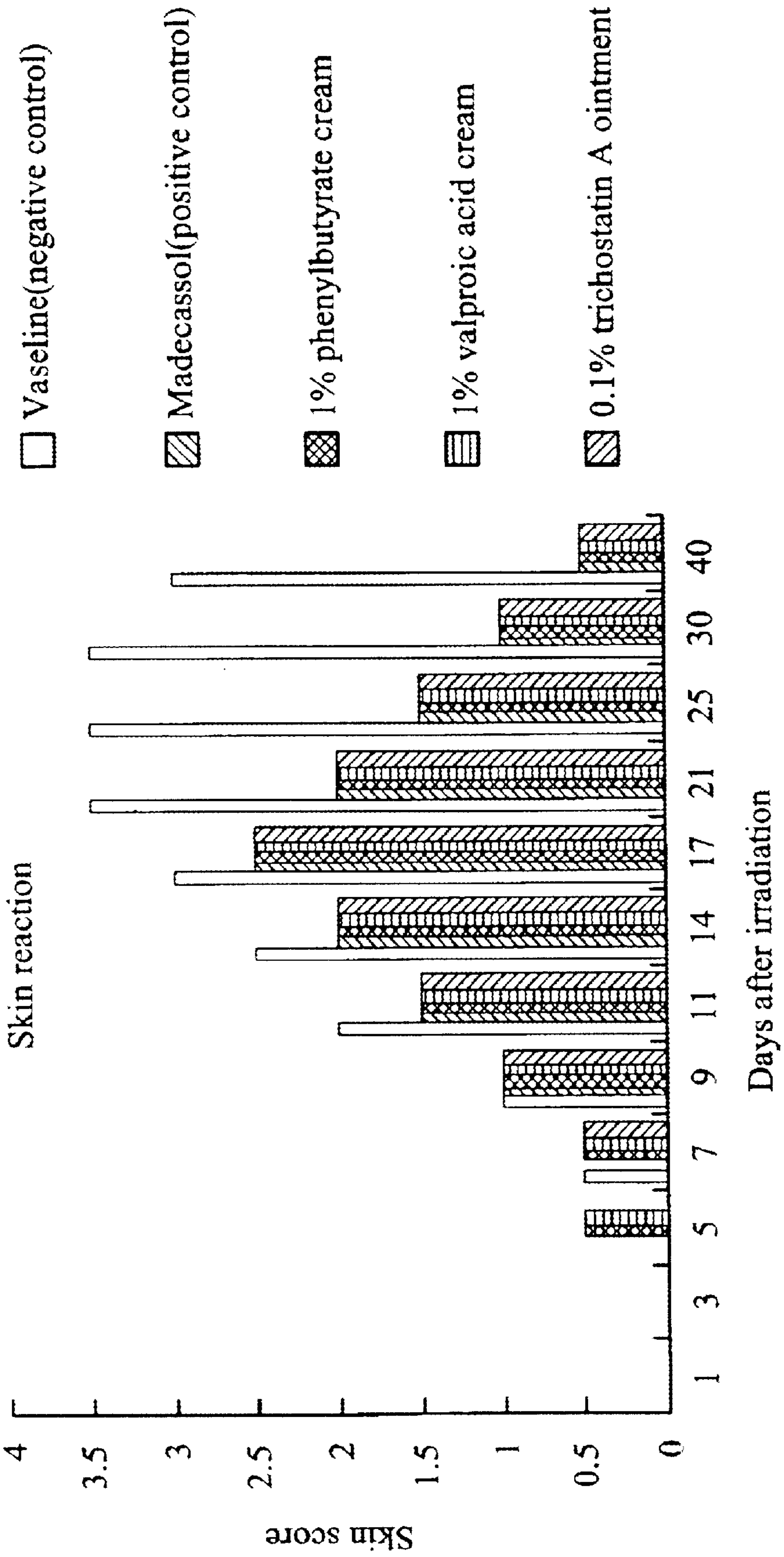
FIG. 1 is a skin reaction score diagram showing the time-course of the average skin score after 40 Gy irradiation. The skin score increases with more severe skin reaction. The skin reactions in the histone deacetylase inhibitor and madecassol groups tended to be less marked than those in the control group. The drug-treated groups also recovered soon.
Figure 2A:
FIGS. 2*a*–2*l* are H&E histology photographs showing that histone deacetylase inhibitors have effects on suppressing radiation cutaneous syndrome. Valproic acid, trichostatin A, and phenylbutyrate have similar effects. One of the treated examples on Day 60 is demonstrated, and compared to the normal skin, acute dermatitis on Day 7, and vehicle group on Day 60.
Figure 2B:
Figure 2C:
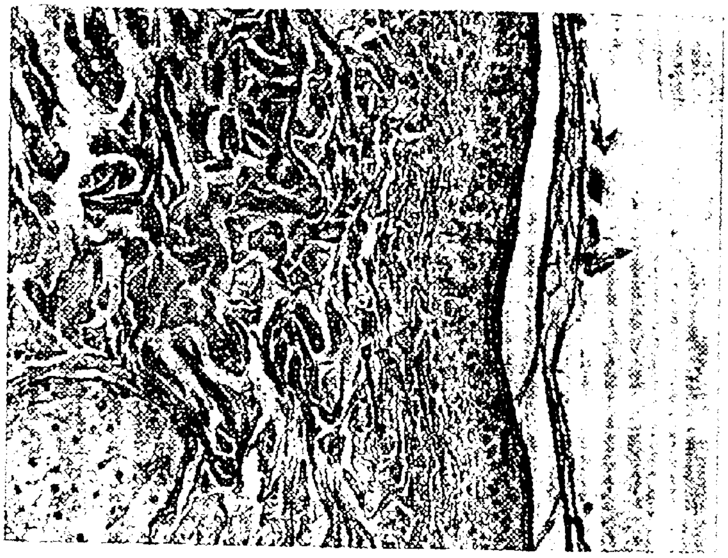
Figure 2D:
Figure 2E:
Figure 2F:
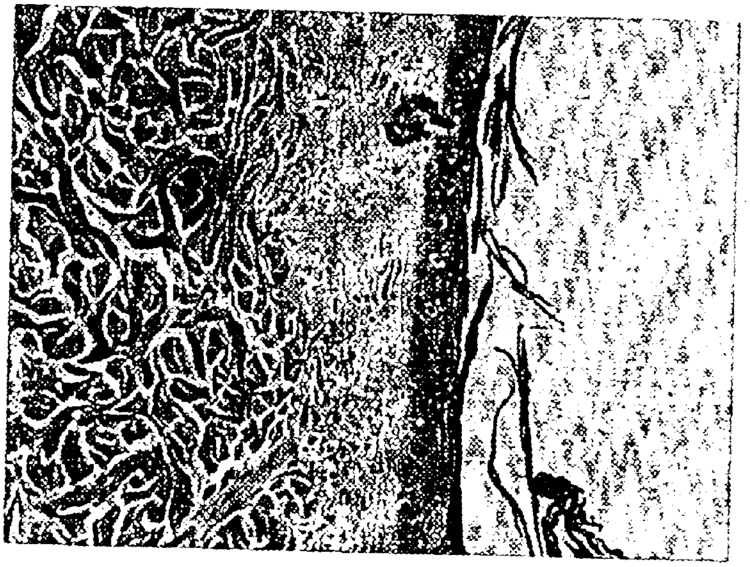
Figure 2G:
Figure 2H:
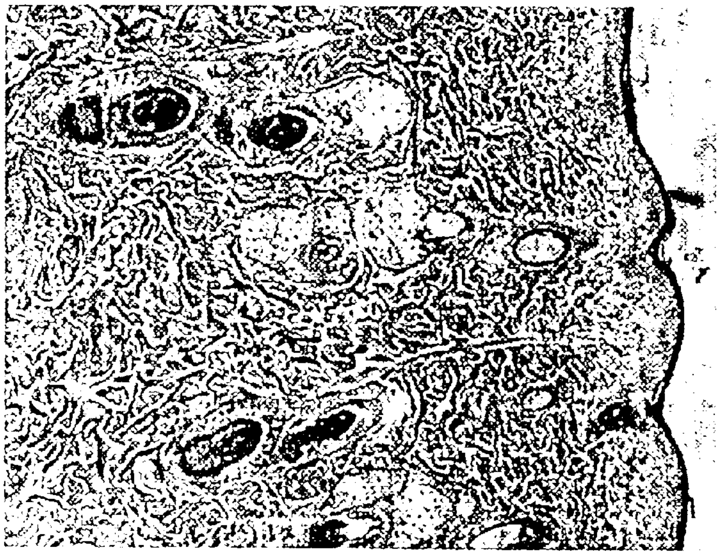
Figure 2I:
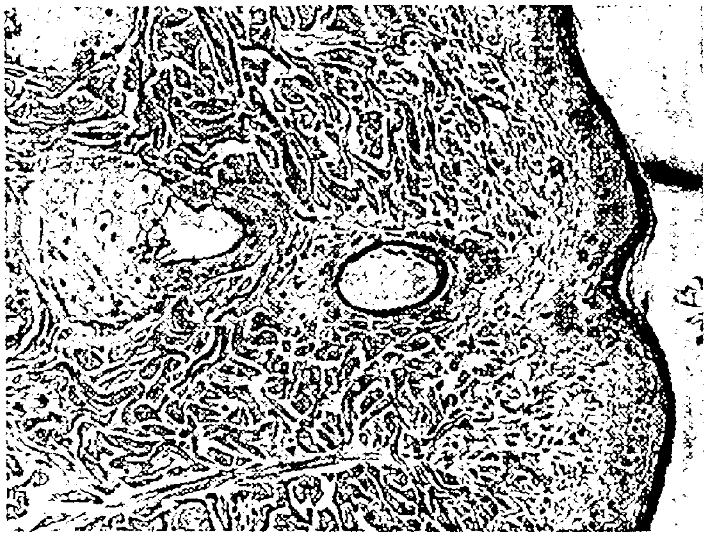
Figure 2J:
Figure 2K:
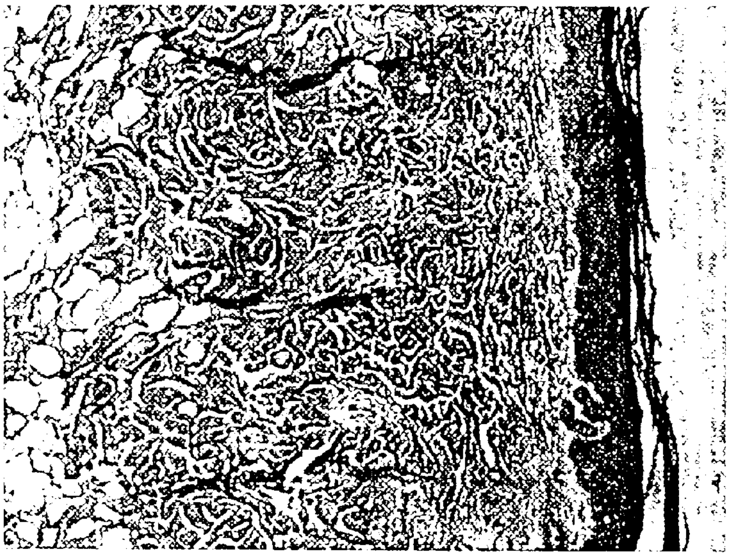
Figure 2L:
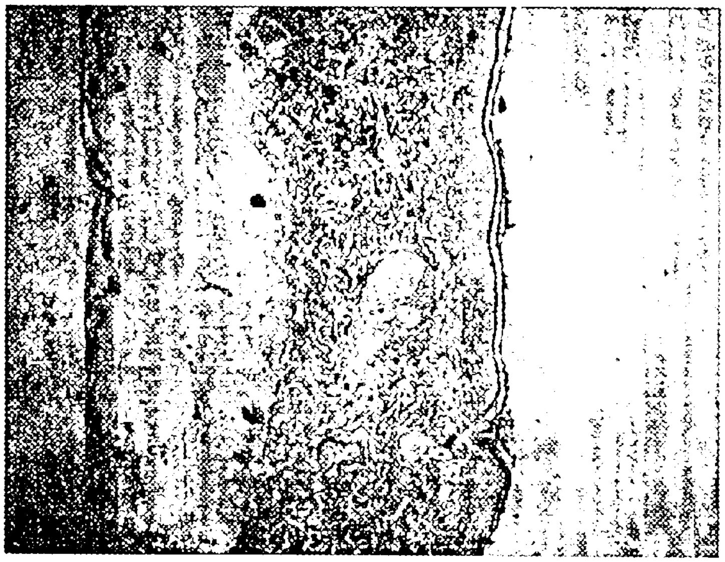

The description in this application is specifically directed to valproic acid, trichostatin A, and phenylbutyrate in radiation cutaneous syndrome, as non-limiting examples and is not intended to limit the scope of the invention.

Valproic acid, trichostatin A and phenylbutyrate or derivatives thereof are disclosed to be useful as agents for treatment in radiation cutaneous syndrome. Pharmaceutical formulations and the use of compounds of valproic acid, trichostatin A and phenylbutyrate are also disclosed.

Trichostatin A (MW 164.21), a hydroxamic acid, is originally isolated from Streptomyces hygroscopicus. Trichostatin A is useful as an antifungal, anticancer, and antiprotozoal agent. Phenylbutyrate (MW 164.21), a natural nontoxic colorless tasteless aromatic fatty acid purified from mammalian urine and plasma, is Food and Drug Administration approved for children with hyperammonemia associated with inborn errors of urea synthesis. Valproic acid is commonly used in treating seizure or migraine.

In the course of experiments valproic acid, trichostatin A and phenylbutyrate were discovered to be histone deacetylase inhibitors strongly affecting decrease of skin swelling, promotion of desquamation healing, and prevention of cutaneous fibrosis in irradiated skin.

The histone deacetylase inhibitor agents can be brought in the form of pharmaceutically acceptable salts. As such they may be used so long as they do not adversely affect the desired pharmacological effects of the compounds. The selection and production can be performed by those skilled in the art. Examples of pharmaceutically acceptable salts include alkali metal salts such as sodium salt or a potassium salt, alkaline earth metal salts such as calcium salt or a magnesium salt, salts with an organic base such as an ammonium salt, or a salt with an organic base such as a triethylamine salt or an ethanolamine salt.

The histone deacetylase inhibitor agents of the present invention may be administered orally or non-orally. In the case of oral administration, they may be administered in the form of soft and hard capsules, tablets, granules, powders, solutions, suspensions or the like. In the case of non-oral administration, they maybe administered in the form of creams, ointments, gels, lotions, patches, suppositories, powder, liposome formations, injection solution, drip infusion formulations or the like, whereby continued membrane absorption can be maintained in the form of solid, viscous liquid, or suspension. The selection of the method for the delivery of these formulations and the vehicles, disintegrators or suspending agents, can be readily made by those skilled in the art. The histone deacetylase inhibitor agents of the present invention may contain a further substance having anti-inflammatory or anti-tumor activities, in addition to valproic acid, trichostatin A, or phenylbutyrate, and a pharmaceutically acceptable carrier or a pharmaceutically acceptable salt thereof.

As recognized by those skilled in the art, the effective doses vary depending on route of administration, excipient usage, and the possibility of co-use with other therapeutic treatments such as the use of other anti-inflammatory or anti-tumor agents. Effective amounts and treatment regimens for any particular subject (e.g., human, dog, or cat) will also depend upon a variety of other factors, including the activity of the specific compound employed, age, body weight, general health status, sex, diet, time of administration, rate of excretion, severity and course of the disease, and the patient's disposition to the disease, but are usually from 0.1 to 50% by weight irrespective of the manner of administration.

In order that the invention described herein may be more readily understood, the following examples are set forth. It should be understood that these examples are for illustrative purposes only and are not to be construed as limiting this invention in any manner. All references cited herein are expressly incorporated by reference in their entirety.

EXAMPLE 1

Various Topical Compositions-Oleaginous Ointment, Cream, and Gel

A. Preparation of an Oleaginous Ointment of Phenylbutyrate 470 g of white petrolatum (Riedel-de Haen), 25 g of paraffin wax 50/52 (local supplier), and 5 g of 4-phenylbutyrate (Merck) were mixed in a beaker and heated at 70° C. to form a paste. The paste was stirred at 400 rpm for 1 hour, and then cooled at room temperature.

B. Preparation of an Oleaginous Ointment of Phenylbutyrate 65 g of white petrolatum (Riedel-de Haen), 15 g of cetyl alcohol (Riedel-de Haen), 260 g of soft paraffin (Merck), 155 g of liquid paraffin (Merck), and 5 g of 4-phenylbutyrate (Merck) were mixed in a beaker and heated at 70° C. to form a paste. The paste was stirred at 400 rpm for 1 hour, and then cooled at room temperature.

C. Preparation of Cream of Phenylbutyrate

Part I: 70 g of Tefose 63®, 20 g of Superpolystate®, 10 g of Coster 5000®, 15 g of Myriyol 318®, 15 g of Coster 5088®, and 15 g of GMS SE® (all commercially available from local supplier) were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), and 149.061 g of deionized water were mixed in a beaker and heated at 70° C.

Part II was slowly added into part I and continually stirred at 400 rpm for 5 minutes to form a mixture. 2% Stabileze QM® (prepared by dissolving 2 g of Stabileze QM® in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

D. Preparation of Gel of Phenylbutyrate

Part I: 10 g of Stabileze QM® and 232.035 g of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 232.035 g of deionized water, and 20 g of 10% NaOH were mixed in a beaker and heated at 70° C.

Part II was slowly added into part I and continually stirred at 400 rpm for 20 minutes to form a mixture. The mixture was cooled at room temperature.

E. Preparation of Gel of Phenylbutyrate

Part I: 10 g of Stabileze QM® and 380.561 g of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 83.5 g of 1,2-propandiol, and 20 g of 10% NaOH were mixed in a beaker and heated at 70° C.

Part II was slowly added into part I and continually stirred at 400 rpm for 20 minutes to form a mixture. The mixture was cooled at room temperature.

F: Preparation of Sustained Release Formulations of Phenylbutyrate

Two formulations were prepared according to the compositions listed in the Table 1.

TABLE 1

Compositions of two sustained release formulations

| Composition | No. of formulation Tri-s-04 | Tri-s-05 |
|---|---|---|
| PF-127 ® (BASE Inc.)* | 2 | 4 |
| Sodium carboxy-methyl cellulose* | 12 | 12 |
| Deionized water | 82.8523 | 80.8523 |
| Sodium 4-phenylbutryate | 1.1477 | 1.1477 |
| 85% phosphoric acid | 2 | 2 |
| PH | 5.93 | 6.01 |

*PF127 ® is the base of the compositions, and sodium carboxymethylcellulose is a thickening agent.

G: Preparation of Liposomal Formulation of Phenylbutyrate

In this liposomal formulation, egg phosphatidylcholine (EPC) and cholesterol were used in equi- or different-molar concentrations as primary lipid components. Various liposomes located with 4-phenylbutyrate were obtained by varying the lipid: phenylbutyrate ratio. Liposomes were prepared by thin film hydration, sized by membrane extrusion, and physically evaluated.

H: Preparation of Ointment of Trichostatin A 472.5 g of white petrolatum (Riedel-de Haen), 27 g of paraffin wax 50/52 (local supplier), and 0.5 g of trichostatin A (sigma) were mixed in a beaker and heated at 70° C. to form a paste. The paste was stirred at 400 rpm for 1 hour, and then cooled at room temperature.

I. Preparation of an Oleaginous Ointment of Trichostatin A 67.5 g of white petrolatum (Riedel-de Haen), 16 g of cetyl alcohol (Riedel-de Haen), 260.5 g of soft paraffin (Merck), 155.5 g of liquid paraffin (Merck), and 0.5 g of trichostatin A (sigma) were mixed in a beaker and heated at 70° C. to form a paste. The paste was stirred at 400 rpm for 1 hour, and then cooled at room temperature.

J. Preparation of Cream of Valproic Acid

Part I: 70 g of Tefose 63®, 20 g of Superpolystate®, 10 g of Coster 5000®, 15 g of Myriyol 318®, 15 g of Coster 5088®, and 15 g of GMS SE® (all commercially available from local supplier) were mixed in a beaker and heated at 70° C.

Part II: 5.739 g of valproic acid (sigma), 0.125 g of methylparaben (Merck), 0.075 g of propylparaben (Merck), and 149.061 g of deionized water were mixed in a beaker and heated at 70° C.

Part II was slowly added into part I and continually stirred at 400 rpm for 5 minutes to form a mixture. 2% Stabileze QM® (prepared by dissolving 2 g of Stabileze QM® in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

EXAMPLE 2

Histone Deacetylase Inhibitors are Effective for Radiation Cutaneous Syndrome

Adult female Sprague Dawley (SD) rats were purchased from the animal center of the National Science Council of Taiwan, and weighed 250–300 g at the time of irradiation. Each rat was caged alone and allowed chow and water. They were anesthetized with pentobarbital 50 mg/kg i.p. before irradiation. The skin over gluteal area was shaved completely and radiation fields with 2-cm diameter were outlined with a marking pen just prior to irradiation. An electron beam with 6 MeV energy produced by a linear accelerator was used. The dose was delivered on Day 0 at 4 Gy/min up to 40 Gy to the prepared area. Each group treated with a histone deacetylase inhibitor was further divided into three subgroups (5 each): one subgroup treated with skin irradiation followed by vehicle, another with skin irradiation followed by a histone deacetylase inhibitor, and the third with skin irradiation only. Then vaseline (negative control), madecassol ointment (positive control), or either vehicles or the 1% phenylbutyrate cream, 1% valproic acid cream, or 0.1% trichostatin A ointment were applied topically to the irradiated skin twice daily from Day 1 to Day 120 after irradiation. The mean dosages of each treatment in the respective groups were 16 mg vaseline per $cm^2$ skin, 16 mg madecassol per $cm^2$ skin, 50 mg phenylbutyrate per $cm^2$ skin, 50 mg valproic acid per $cm^2$ skin, 5 mg trichostatin A per $cm^2$ skin, and an equivalent amount of the vehicle base for the control groups. The gross skin reactions were evaluated in all rats. Acute skin reactions were evaluated and scored every other day until the $30^{th}$ day after irradiation using the modified skin score system (Abe Y. and Urano M. Fraction size-dependent acute skin reaction of mice after multiple twice-a-day doses. International Journal of Radiation Oncology, Biology, Physics. 18(2):359–64, 1990): 0=normal, 0.5=slight epilation, 1.0=epilation in about 50% of the radiated area, 1.5=epilation in greater than 50% of the area, 2.0=complete epilation, 2.5=complete epilation with definitive edema or dry desquamation in more than 50% of the area, 3.0=moist desquamation in a small area, 3.5=moist desquamation in most of the area. Five rats in each group underwent skin histological examination from Day 1 to Day 130. Each specimen was embedded in a paraffin block and thin sections were prepared, stained by the hematoxylin eosin method and examined under a light microscope.

The skin score increases with more severe skin reaction. The average skin reaction scores in each group are shown in FIG. 1. On Day 11, the skin reactions in the groups treated with madecassol (positive control) or histone deacetylase inhibitors were less marked than those in the negative or vehicle control groups. By day 21, the epilation in the negative or vehicle groups had progressed to wet desquamation in most areas whereas in the madecassol or histone deacetylase inhibitor groups, it improved, and epithelium healing had begun quickly.

TABLE 2

| Treatment group | Summary of histological findings in irradiated skin treated with or without histone deacetylase inhibitors (Day 1–130) | | | | | | | |
|---|---|---|---|---|---|---|---|---|
| | Skin reaction | | | | | | | |
| | Day 1–21 | | | Day 22–40 | | Day 41–130 | | |
| | A | B | C | D | E | F | G | H |
| Vaseline | +++++ | +++++ | +++ | +++++ | + | | +++++ | ++ |
| Madecassol | ++ | ++++ | | ++ | + | ++ | +++ | |
| Cream vehicle | +++++ | +++++ | ++ | +++++ | + | | +++++ | ++ |
| 1% phenylbutyrate cream | ++++ | ++++ | | + | +++++ | +++++ | | |
| 1% valproic acid cream | ++++ | ++++ | | + | +++++ | +++++ | | |
| Ointment vehicle | +++++ | +++++ | +++ | +++++ | + | | +++++ | ++ |
| 0.1% trichostatin A ointment | ++ | ++ | | + | +++++ | +++++ | | |

*The histological findings on skin specimens from 5 irradiated rats in each group are represented as follows: A, subepithelial swelling. B, dry desquamation. C, wet desquamation. D, atrophy of epidermis in most areas. E, atrophy of skin appendages in most areas. F, increased thickness of epithelium. G, dermal fibrosis, more vessel density, and increased thickness of dermis. H, chronic ulceration, or necrosis and bullae formation of the epidermis near the ulcer. The "+" to "+++++" means specimens from one to five rats showed the reaction as indicated.

Referring to the Table 2, there are apparent changes in the histological findings between the control and the groups treated with histone deacetylase inhibitors. It was observed that the rats of the vehicle groups had subepidermal edematous change, complete epilation, thinner epidermis, increased thickness of dermis due to more fibroblasts and collagen deposit, and higher density of proliferative neovessels and skin appendage, which is similar to the negative control (the vaseline group and the radiation alone group). In contrast, the rats treated with histone deacetylase inhibitors had thicker epidermis with more cell layers but without dermal fibrosis. The thickness and feature of dermis in the treated groups were almost the same as those in normal skin except scarce skin appendage. Moreover, on Day 130, skin samples taken from the groups treated with histone deacetylase inhibitors had softer and thinner dermis and less capillary bleeding, while skin samples taken from the other two groups had rigid thick dermis and were oozing.

Taken together, the above results indicate that histone deacetylase inhibitors have therapeutic effects not only on the radiation-induced acute reactions of swelling and desquamation but also on the late sequela of radiation dermal fibrosis, ulceration and necrosis.

EXAMPLE 3

H&E Histology of Irradiated Skin Treated with or without Histone Deacetylase Inhibitors Valproic acid, trichostatin A, and phenylbutyrate are structurally unrelated histone deacetylase inhibitors, and all have the similar effects on suppressing the radiation cutaneous syndrome including acute dermatitis and desquamation, and late fibrosis, ulceration and necrosis. As shown in FIG. 2, the groups treated with histone deacetylase inhibitors for 60 days have thicker epidermis with more cell layers but have thinner dermis (measured from epidermis to the subcutaneous fat layer) with less collagen deposition when compared to the vehicle group on Day 60 and the control groups (normal skin and acute reaction on Day 7).

EXAMPLE 4

Figure 3A:
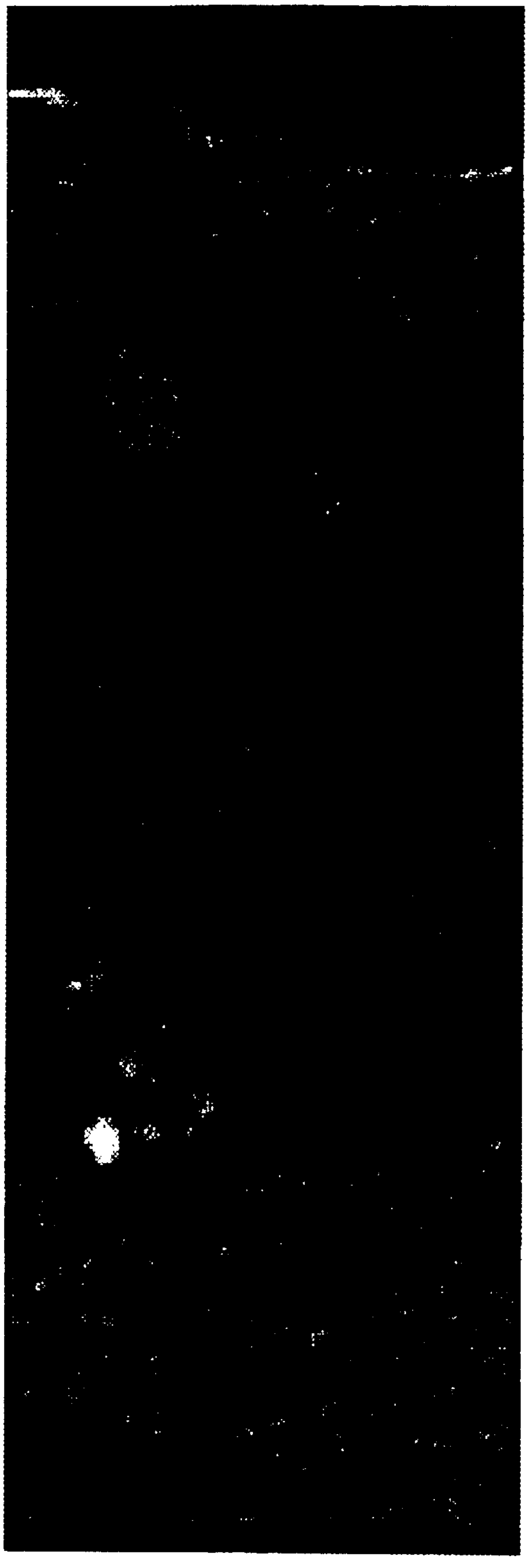
FIGS. 3*a*–3*c* are photographs of immunofluorescence with the anti-TGF-beta antibody showing that the expression of TGF-beta, a fibrogenic growth factor, was suppressed by the histone deacetylase inhibitor in example 3.
Figure 3B:
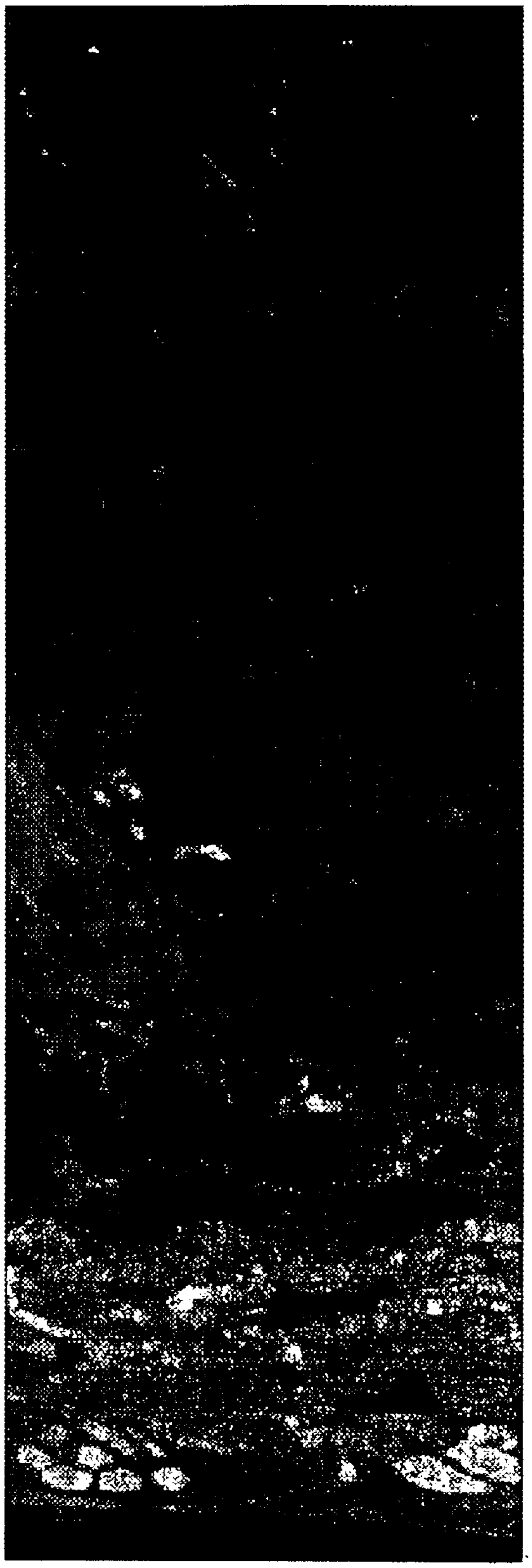
Figure 3C:
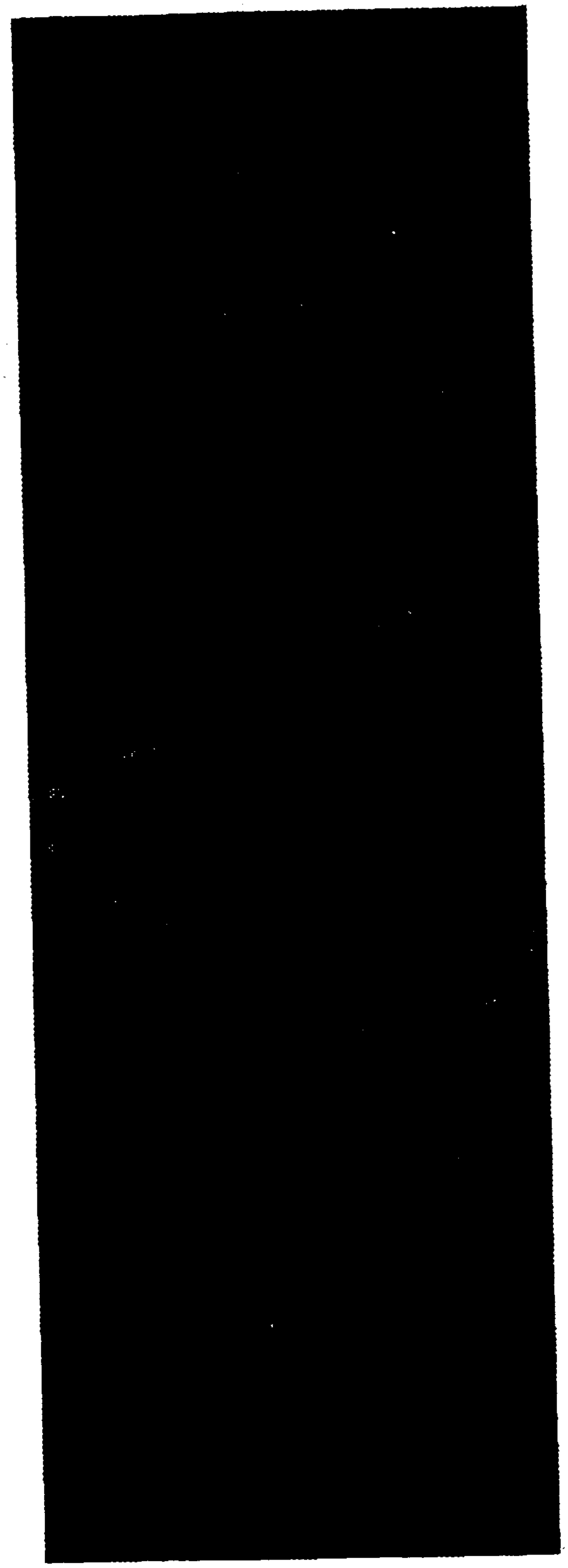

Immunofluorescence of TGF-beta Expression, a Fibrogenic Growth Factor, in Irradiated Skin Treated with the Histone Deacetylase Inhibitor The same pathological sections in example 3 were subjected to immunofluorescence with the anti-TGF-beta antibody. As shown in FIG. 3, the TGF-beta protein, a strong fibrogenic factor, was upregulated by irradiation, and highly expressed in fibrogenic skin both in keratinocytes of the epidermis and in myofibroblasts of the dermis on Day 60, but the expression of TGF-beta was suppressed effectively in the histone deacetylase inhibitor treated group on Day 60.

EXAMPLE 5

Figure 4A:
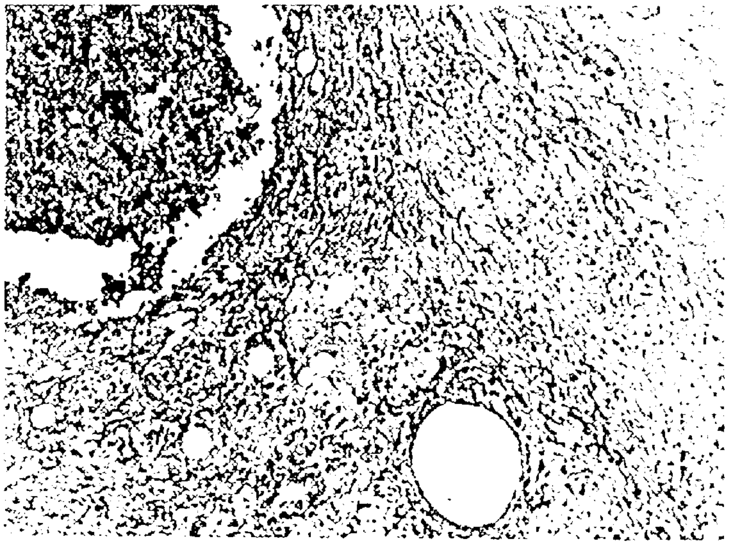
FIGS. 4*a*–4*b* are photographs of immunohistochemistry with the anti-TNF-α antibody showing that the expression of TNF-α, an inflammatory cytokine, was suppressed by the histone deacetylase inhibitor.
Figure 4B:

Immunohistochemistry of TNF-α Expression, an Inflammatory Cytokine, in Irradiated Skin Treated with or without the Histone Deacetylase Inhibitor The pathological sections taken from the rats treated with or without the histone deacetylase inhibitor up to 130 days were subjected to immunohistochemistry with the anti-TNF-α antibody. As shown in FIG. 4, TNF-α was highly upregulated in the subcutaneous tissue having chronic ulcerations and necrosis in the rat of the vehicle group on Day 130 (one example with severe radiation skin damage in the vehicle group). In contrast, TNF-α was suppressed in the histone deacetylase inhibitor group, and there was no skin ulceration in the drug-treated group on Day 130.

In conclusion, at least three unrelated histone deacetylase inhibitors are active compounds for the treatment of radiation cutaneous syndrome including acute dermatitis and desquamation, and late fibrosis, ulceration and necrosis. The present invention also relates to a method for the treatment of humans or animals afflicted with radiation exposure or radiotherapy, comprising administering to the subject an effective amount of a histone deacetylase inhibitor in particular valproic acid, trichostatin A and phenylbutyrate or a pharmaceutically acceptable salt thereof and optionally a suitable excipent.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally and functionally analogous to histone deacetylase inhibitors described above can also be used to practice the present invention. Thus, other embodiments are also within the claims.

What is claimed is:

1. A method for treating radiation-induced skin damage, comprising administration to humans or animals in need of treatment for radiation-induced dermatitis, desquamation, fibrosis, ulceration, or necrosis a therapeutically effective amount of a pharmaceutical composition comprising a histone deacetylase inhibitor and a pharmaceutically acceptable carrier or a pharmaceutically acceptable salt thereof.

2. The method as claimed in claim 1, wherein the histone deacetylase inhibitor is present in an amount from 0.1 to 50% by weight of the compositions.

3. The method as claimed in claim 1, wherein the histone deacetylase inhibitor is present in an amount from 0.01 to 100 mg of the histone deacetylase inhibitor.

4. The method as claimed in claim 1, wherein the histone deacetylase inhibitor comprises valproic acid or a pharmaceutically acceptable salt thereof.

5. The method as claimed in claim 1, wherein the histone deacetylase inhibitor comprises trichostatin A or a pharmaceutically acceptable salt thereof.

6. The method as claimed in claim 1, wherein the histone deacetylase inhibitor comprises phenylbutyrate or a pharmaceutically acceptable salt thereof.

7. The method as claimed in claim 1, wherein the histone deacetylase inhibitor comprises depudecin or a pharmaceutically acceptable salt thereof.

8. The method as claimed in claim 1, wherein the histone deacetylase inhibitor comprises trapoxin A or a pharmaceutically acceptable salt thereof.

9. The method as claimed in claim 1, wherein the histone deacetylase inhibitor comprises depsipeptide or a pharmaceutically acceptable salt thereof.

10. The method as claimed in claim 1, wherein the histone deacetylase inhibitor comprises oxamflatin or a pharmaceutically acceptable salt thereof.

11. The method as claimed in claim 1, wherein the histone deacetylase inhibitor comprises benzamide or a pharmaceutically acceptable salt thereof.

12. The method as claimed in claim 1, wherein the pharmaceutical composition is administered non-orally.

13. The method as claimed in claim 12, wherein the composition is a cream, an ointment, a gel, a lotion, a patch, a suppository, a powder form, a liposome formation, an injection solution, or a drip infusion.

* * * * *